US010563260B2

(12) United States Patent
Lavedan et al.

(10) Patent No.: US 10,563,260 B2
(45) Date of Patent: Feb. 18, 2020

(54) METHOD OF PREDICTING A PREDISPOSITION TO QT PROLONGATION

(71) Applicant: Vanda Pharmaceuticals, Inc., Washington, DC (US)

(72) Inventors: Christian Lavedan, Potomac, MD (US); Simona Volpi, Derwood, MD (US); Louis Licamele, Potomac, MD (US)

(73) Assignee: VANDA PHARMACEUTICALS, INC., Washington, DC (US)

( * ) Notice: Subject to any disclaimer, the term of this patent is extended or adjusted under 35 U.S.C. 154(b) by 67 days.

(21) Appl. No.: 15/705,054

(22) Filed: Sep. 14, 2017

(65) Prior Publication Data
US 2018/0002757 A1   Jan. 4, 2018

Related U.S. Application Data

(63) Continuation of application No. 14/694,135, filed on Apr. 23, 2015, now abandoned, which is a continuation of application No. 13/263,075, filed as application No. PCT/US2010/029931 on Apr. 5, 2010, now Pat. No. 9,074,255.

(60) Provisional application No. 61/167,138, filed on Apr. 6, 2009.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| 5,364,866 | A | 11/1994 | Strupczewski et al. |
| 5,658,911 | A | 8/1997 | Strupczewski et al. |
| 6,140,345 | A | 10/2000 | Strupczewski et al. |
| 2006/0073506 | A1* | 4/2006 | Christians ............ C12Q 1/6813 435/6.11 |
| 2011/0077539 | A1 | 3/2011 | George et al. |

FOREIGN PATENT DOCUMENTS

| WO | 9309276 A1 | 5/1993 |
| WO | 9511680 A1 | 5/1995 |
| WO | 0124681 A1 | 4/2001 |
| WO | 0124681 A2 | 4/2001 |
| WO | 0179554 A1 | 10/2001 |
| WO | 03016504 A2 | 2/2003 |
| WO | 03016504 A1 | 3/2003 |
| WO | 03020707 A1 | 3/2003 |
| WO | 03062791 A1 | 7/2003 |
| WO | 03062791 A2 | 7/2003 |
| WO | 2004057030 A1 | 7/2004 |
| WO | 2004057030 A2 | 7/2004 |
| WO | 2006039663 A2 | 4/2006 |
| WO | 2006039663 A3 | 11/2006 |
| WO | 2006124646 A2 | 11/2006 |
| WO | 2006131528 A2 | 12/2006 |
| WO | 2006131528 A3 | 3/2007 |
| WO | 2006124646 A3 | 8/2007 |

OTHER PUBLICATIONS

Mueller, Frank, Patent Application No. 10713287.0 Office Action dated Jun. 11, 2014, 6 pages.
Levine et al., "Iloperidone: A novel atypical antipsychotic for the treatment of schizophrenia," 2008, pp. 1-7, Formulary Journal.
Volpi et al., "Pharmacogenomic analysis shows differences between markers associated with responses of two atypical antipsychotics, iloperidone and ziprasidone, in the treatment of patients with schizophrenia," 2007, Abstsract, 57 Annual Meeting of the American Society of Human Genetics.
Sitton, Office Action Communication for U.S. Appl. No. 13/263,076 dated Nov. 29, 2013, 24 pages.
Sitton, Office Action Communication for U.S. Appl. No. 13/263,077 dated Nov. 7, 2013, 25 pages.
Ss66391863, rs7067971, dbSNP Short Genetic Variations, NCBI, NLM, 2006, 3 pages.
Ss66046634, rs1083338, dbSNP Short Genetic Variations, NCBI, NLM, 2007, 5 pages.
Chiang et al., "The Long QT Syndromes: Genetic Basis and Clinical Implications," Jul. 2000, pp. 1-12, Journal of American College of Cardiology, vol. 36, No1 1 (XP002590440).
Donger et al., "KVLQT1 C-Terminal Missense Mutation Causes a Forme Fruste Long-QT Syndrome," Nov. 1997, pp. 2778-2781, American Heart Association, vol. 96, No. 9 (XP002922668).
Liu et al., "KCNQ1 and KCNH2 Mutations Associated with Long QT Syndrome in a Chinese Population," Nov. 2002, pp. 1-7, Human Mutation, Mutation in Brief, vol. 20, No. 6 (XP002590441).
Volpi et al., "Whole Genome Association Study Identities Polymorphisms Associated with QT Prolongation During Iloperidone Treatment of Schizophrenia," Jun. 2008, pp. 1024-1031, Molecular Psychiatry, vol. 14, No. 11 (XP002590482).
Yang et al., "Allelic Variants in Long-QT Disease Genes in Patients With Drug-Associated Torsades de Pointes," Apr. 2002, pp. 1943-1948, Circulation downloaded from: circ.ahajournals.org at the European Patent Office.
Patent Cooperation Treaty, PCT Notification of Transmittal of the International Search Report and the Written Opinion of the International Searching Authority, or the Declaration for PCT/US2010/029921 dated Aug. 19, 2010, 15 pages.

(Continued)

*Primary Examiner* — Jehanne S Sitton
(74) *Attorney, Agent, or Firm* — Hoffman Warnick LLC

(57) ABSTRACT

The present invention describes an association between genetic polymorphisms in the FAM13A1 (family with sequence similarity 13, member A1) gene and a predisposition to prolongation of the QT interval, and provides related methods for the prediction of such a predisposition, the administration of QT interval-prolonging compounds to individuals having such a predisposition, and determining whether a compound is capable of inducing QT prolongation.

10 Claims, No Drawings

(56) References Cited

OTHER PUBLICATIONS

Cohen et al., "Cloning and Characterization of FAM13A1—A Gene Near a Milk Protein QTL on BTA6: Evidence for Popluation-Wide Linkage Disequilibrium in Israeli Holsteins," Aug. 2004, pp. 374-383, Genomics 84, Academic Press, available online at: www.sciencedirect.com.
Patent Cooperation Treaty, PCT Notification of Transmittal of the International Search Report and the Written Opinion of the International Searching Authority, or the Declaration for PCT/US2010/029931 dated May 27, 2010, 13 pages.
Cascorbi, "Role of Pharmacogenetics of ATP-Binding Cassette Transporters in the Pharmacokinetis of Drugs," Nov. 2006, pp. 457-473, Pharmacology & Therapeutics, Science Direct, vol. 112, No. 2.
Patent Cooperation Treaty, PCT Notification of Transmittal of the International Search Report and the Written Opinion of the International Searching Authority, or the Declaration for PCT/US2010/029943 dated Jul. 5, 2010, 14 pages.
Fujita et al., "Association of ATP-Binding Cassette, Sub-Family C, No. 2 (ABCC2) Genotype with Pharmacokinetics of Irinotecan in Japanese Patients with Metastatic Colorectal Cancer Treated with Irinotecan Plus Infusional 5-Fluorouracil/Leucovorin (FOLFIRI)," Nov. 2008, pp. 2137-2142, Biological & Pharmaceutical Bulletin, vol. 31, No. 11 (XP007913544).
Derosse et al., "The Genetics of Symptom-Based Phenotypes: Toward a Molecular Classification of Schizophrenia," Jul. 2008, pp. 1047-1043, Schizophrenia Bulletin, vol. 34, No. 6 (XP007913527).
Patent Cooperation Treaty, PCT Notification of Transmittal of the International Search Report and the Written Opinion of the International Searching Authority, or the Declaration for PCT/US2010/029945 dated Jul. 7, 2010, 13 pages.
Sitton, Office Action Communication for U.S. Appl. No. 13/263,074 dated Jan. 13, 2014, 28 pages.
GenBank, *Homo sapiens* KVLQt1 Gene, GenBank:AJ006345.1, NCBI, 88 pages.
Sitton, Office Action Communication for U.S. Appl. No. 13/263,076 dated Mar. 27, 2014, 11 pages.
Sitton, Office Action Communication for U.S. Appl. No. 13/263,077 dated Mar. 27, 2014, 11 pages.
U.S. Appl. No. 14/694,141, Final Office Action 1 dated Oct. 8, 2015, 14 pages.
U.S. Appl. No. 14/694,142, Final Office Action 1 dated Oct. 8, 2015, 14 pages.
U.S. Appl. No. 14/694,141, Final Office Action 2 dated Aug. 24, 2016, 26 pages.
Terwilliger, et al., "An utter refutation of the 'Fundamental Theorem of the HapMap,'" European Journal of Human Genetics, (14): pp. 426-437 (2006).
Sotos, et al., "The Transitivity Misconception of Pearson's Correlation Coefficient," Statistics Education Research Journal, 8(2): pp. 33-55 (2009).
Wall, et al. "Haplotype Blocks and Linkage Disequilibrium in the Human Genome," Nature Reviews-Genetics, (4): pp. 587-597 (2003).
Notice of Allowance and Fee(s) Due for U.S. Appl. No. 14/632,914, dated Jun. 1, 2015, 8 pages.
Office Action for U.S. Appl. No. 14/694,141, dated Jun. 9, 2015, 27 pages.
Office Action for U.S. Appl. No. 14/694,142, dated Jun. 18, 2015, 28 pages.
Final Office Action for U.S. Appl. No. 14/694,141, dated Oct. 8, 2015, 14 pages.
Final Office Action for U.S. Appl. No. 14/694,142, dated Oct. 8, 2015, 14 pages.
Cussac, International Application No. PCT / US2010 / 029931, PCT International Preliminary Report on Patentability, dated Apr. 6, 2009, 7 pages.
Nickitas-Etienne, International Application No. PCT / US2010 / 029945, PCT International Preliminary Report on Patentability, dated Apr. 6, 2009, 7 pages.
Nickitas-Etienne, International Application No. PCT / US2010 / 029943, PCT International Preliminary Report on Patentability, dated Apr. 6, 2009, 7 pages.
Lindner, International Application No. PCT / US2010 / 029921, PCT International Preliminary Report on Patentability, dated Apr. 6, 2009, 7 pages.
Cohen et al., "Cloning and Characterization of FAM13A1—A Gene Near a Milk Protein QTL on BTA6: Evidence for Population-Wide Linkage Disequilibrium in Israeli Holsteins," Aug. 2004, pp. 374-383, Genomics 84, Academic Press, available online at: www.sciencedirect.com.
Hegele, "SNP Judgments and Freedom of Association," 2003, pp. 1058-1061, Arteriosclerosis, Thrombosis, and Vascular Biology, vol. 22.
Juppner, "Functional Properties of the PTH/PTHrP Receptor," 1995, pp. 39S-42S, Bone, vol. 17, No. 2.
Lucentini, "Gene Association Studies Typically Wrong," 2004, p. 20, The Scientist, vol. 24.
Ss66324480, rs3775378, dbSNP Short Genetic Variations, NCBI, NLM, 2006, 5 pages.
Volpi et al., "Pharmacogenomic analysis shows differences between markers associated with responses of two atypical antipsychotics, iloperidone and ziprasidone, in the treatment of patients with schizophrenia," 2007, Abstract, 57 Annual Meeting of the American Society of Human Genetics.
Volpi et al., "Whole Genome Association Study Identifies Polymorphisms Associated with QT Prolongation During Iloperidone Treatment of Schizophrenia," Jun. 2008, pp. 1024-1031, Molecular Psychiatry, vol. 14, No. 11 (XP002590482).
Sitton, Office Action Communication for U.S. Appl. No. 13/263,075 dated Oct. 8, 2013, 23 pages.
Albers et al., "Iloperidone: a new benzisoxazole atypical antipsychotic drug. Is it novel enough to impact the crowded atypical antipsychotic market?" Expert Opin Investig Drugs. 17(1):61-75 (2008).
Sitton, Office Action Communication for U.S. Appl. No. 13/263,075 dated Mar. 20, 2014, 11 pages.
Genbank Accession No. AJ006345.1, NCBI, NLM; 2006.
Sitton, Office Action Communication for U.S. Appl. No. 13/263,074, dated Oct. 2, 2014, 18 pages.
Sitton, Office Action Communication for U.S. Appl. No. 13/263,075, dated Oct. 3, 2014, 19 pages.
Sitton, Office Action Communication for U.S. Appl. No. 13/263,076, dated Oct. 3, 2014, 19 pages.
Sitton, Office Action Communication for U.S. Appl. No. 13/263,077, dated Oct. 3, 2014, 19 pages.
Sitton, Notice of Allowance and Fee(s) Due for U.S. Appl. No. 13/263,074, dated Feb. 11, 2015, 15 pages.
Sitton, Notice of Allowance and Fee(s) Due for U.S. Appl. No. 13/263,075, dated Mar. 6, 2015, 7 pages.
Sitton, Notice of Allowance and Fee(s) Due for U.S. Appl. No. 13/263,076, dated Mar. 10, 2015, 11 pages.
Sitton, Notice of Allowance and Fee(s) Due for U.S. Appl. No. 13/263,077, dated Mar. 13, 2015, 7 pages.

* cited by examiner

METHOD OF PREDICTING A PREDISPOSITION TO QT PROLONGATION

CROSS-REFERENCE TO RELATED APPLICATIONS

This application is a continuation of co-pending U.S. application Ser. No. 14/694,135, filed Apr. 23, 2015, which is a continuation of then-co-pending U.S. application Ser. No. 13/263,075, filed Oct. 5, 2011, which is a US National Stage application under 35 USC 371 of PCT/US2010/029931, filed Apr. 5, 2010, which claims the benefit of U.S. Provisional Patent Application No. 61/167,138, filed Apr. 6, 2009, each of which is incorporated by reference as though fully set forth herein.

BACKGROUND OF THE INVENTION

1. Technical Field

The invention relates generally to a method of predicting an individual's predisposition to QT prolongation, and more particularly, to a method of predicting such predisposition based on a sequence of the individual's FAM13A1 (family with sequence similarity 13, member A1) gene.

2. Background

Prolongation of the electrocardiographic QT interval (the time between the start of the Q wave and the end of the T wave) is referred to as long QT syndrome (LQTS). LQTS may comprise a genetic component. In some patients with LQTS, OT prolongation can be a chronic condition. In some persons, LQTS may be induced by the administration of an active pharmaceutical ingredient that prolongs the QT interval. A number of compounds are believed to be capable of prolonging the QT interval. These include amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, and thioridazine.

Other compounds are suspected of being capable of prolonging the QT interval, although such prolongation has not been definitively established. These include alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, and ziprasidone.

Individuals at risk of suffering LQTS are advised not to use still other compounds, due to the possibility that they may prolong the QT interval. These include albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, and trimipramine.

The FAM13A1 gene has been mapped by Cohen et al. to 4q22.1 and determined to contain 18 exons. Cohen et al., *Cloning and characterization of FAM13A1-a gene near a milk protein QTL on BTA6: evidence for population-wide linkage disequilibrium in Israeli Holsteins*, Genomics 2004 August; 84(2):374-83 PubMed ID: 15234000. Cohen et al. cloned the first member of a novel gene family (FAM13) in bovine. This gene is neighboring an extracellular matrix (ECM) cluster. This cluster of genes containing sequence motifs essential for integrin-receptor interactions is located on HSA4q21 and on BTA6, within the critical region of a quantitative trait locus (QTL) affecting milk protein production. Genes within this cluster are involved in the formation of bone and lobuloalveolar structures in mammary gland and in kidney function.

SUMMARY OF THE INVENTION

The present invention describes an association between genetic polymorphisms in the FAM13A1 (family with sequence similarity 13, member A1) gene and a predisposition to prolongation of the QT interval, and provides related methods for the diagnosis of such predisposition and for the administration of QT interval-prolonging compounds to individuals having such a predisposition.

A first aspect of the invention provides a method of administering to an individual a compound capable of prolonging the individual's QT interval, the method comprising determining at least a portion of an individual's FAM13A1 (family with sequence similarity 13, member A1) gene sequence; and in the case that a portion of the individual's FAM13A1 sequence is associated with an increased risk of QT prolongation, administering to the individual a quantity of the compound less than would be administered to an individual having a FAM13A1 gene sequence not associated with an increased risk of QT prolongation, or electing instead to treat the individual with a different compound not known to be associated with QT prolongation.

A second aspect of the invention provides a method of determining whether or not an individual is predisposed to prolongation of the QT interval, the method comprising: determining at least a portion of an individual's FAM13A1 (family with sequence similarity 13, member A1) gene sequence.

A third aspect of the invention provides a method of administering a compound capable of prolonging a QT interval to an individual suffering from long QT syndrome (LQTS), the method comprising: determining at least a portion of an individual's FAM13A1 (family with sequence similarity 13, member A1) gene sequence; and administering to the individual a quantity of the compound based on the individual's FAM13A1 gene sequence.

A fourth aspect of the invention provides a method of administering to an individual a compound capable of prolonging the individual's QT interval, the method comprising: characterizing an expression product of an individual's FAM13A1 (family with sequence similarity 13, member A1) gene; and in the case that the characterized expression product is associated with an increased risk of QT prolongation, administering to the individual a quantity of the compound less than would be administered to an individual having an expression product not associated with an increased risk of QT prolongation. Expression products of the FAM13A1 gene may include, for example, mRNA and protein including any isoform of the mRNA and protein.

A fifth aspect of the invention provides a method of determining whether an individual is predisposed to prolongation of the QT interval, the method comprising: characterizing an expression product of an individual's FAM13A1 (family with sequence similarity 13, member A1) gene.

A sixth aspect of the invention provides a method of administering a compound capable of prolonging a QT interval to an individual suffering from long QT syndrome (LQTS), the method comprising: characterizing an expression product of an individual's FAM13A1 (family with sequence similarity 13, member A1) gene; and administering to the individual a quantity of the compound based on the characterized expression product.

A seventh aspect of the invention provides a method of determining whether a compound is capable of prolonging QT interval in an individual, the method comprising: measuring an expression product of the individual's FAM13A1 (family with sequence similarity 13, member A1) gene; administering to the individual a quantity of the compound; re-measuring the expression product of the individual's FAM13A1 gene; and determining whether the compound is capable of prolonging the individual's QT interval based on a difference in the measurements of the expression product of the individual's FAM13A1 gene.

An eighth aspect of the invention provides a method of determining whether a compound is capable of prolonging a QT interval in an individual, the method comprising: measuring a QT interval of each of a plurality of test organisms, the plurality including a first test organism having a FAM13A1 (family with sequence similarity 13, member A1) genotype associated with a predisposition for prolongation of QT interval and a second organism having FAM13A1 genotype not associated with a predisposition for prolongation of QT interval; administering a quantity of the compound to each of the plurality of test organisms; remeasuring a QT interval of at least the first test organism; and determining that the compound is capable of prolonging a QT interval in an individual in the case that the remeasured QT interval is greater than the measured QT interval. Test organisms may include, for example, humans, animal models, and/or cell lines.

DETAILED DESCRIPTION OF THE INVENTION

As indicated above, the invention provides a method of predicting an individual's predisposition to QT prolongation based on the sequence of the individual's FAM13A1 (family with sequence similarity 13, member A1) gene.

At least one single nucleotide polymorphisms (SNPs) within the FAM13A1 gene has been found to have a significant correlation to a predisposition to drug-induced QT prolongation. Table 1, below, shows such SNPs and the genotypes associated with QT prolongation following the administration of iloperidone.

TABLE 1

FAM13A1 SNP Genotypes and QT Prolongation Following Administration of Iloperidone

| Affymetrix SNP No. | rs_number[1] | Position[2] | Lowest QTc change | P value[3] | Allele A | Allele B |
|---|---|---|---|---|---|---|
| SNP_A-4194821 | rs2924941 | 89863220 | AA | 0.809963782 | C | T |
| SNP_A-2093666 | rs3017895 | 89868514 | BB | 0.530500186 | C | T |
| SNP_A-1977994 | rs17014483 | 89886614 | non-BB | 0.128385989 | C | T |
| SNP_A-2306584 | rs7683339 | 89891505 | AB | 0.090492451 | C | T |
| SNP_A-2162316 | rs6841084 | 89914508 | AB | 0.507117232 | A | T |
| SNP_A-4296194 | rs12507401 | 89915913 | non-AA | 0.064868339 | C | G |
| SNP_A-4283738 | rs17014546 | 89916235 | AA | 0.018465115 | C | T |
| SNP_A-1943446 | rs17014602 | 89950009 | non-AA | 0.257980315 | C | G |
| SNP_A-2065917 | rs4544678 | 89950302 | AA | 0.035706045 | A | G |
| SNP_A-1808669 | rs7691186 | 89950932 | AA | 0.039030668 | A | G |
| SNP_A-2067635 | rs6814344 | 89952905 | BB | 0.018558356 | C | T |
| SNP_A-2251180 | rs13131633 | 89958502 | BB | 0.022420846 | A | G |
| SNP_A-1906173 | rs3775378 | 89959101 | non-BB | 1.58682E−07 | C | T |
| SNP_A-2200417 | rs2305934 | 89963265 | BB | 0.048871501 | A | G |
| SNP_A-4243899 | rs9991039 | 89984895 | AA | 0.869452703 | A | T |
| SNP_A-4290819 | rs17014687 | 89985586 | non-BB | 0.010624243 | C | T |
| SNP_A-1870378 | rs1379932 | 90019915 | AA | 0.310046334 | C | T |
| SNP_A-2200089 | rs1458551 | 90031265 | AA | 0.437083654 | C | T |
| SNP_A-4287986 | rs2609265 | 90045989 | nonAB | 0.05605724 | C | T |
| SNP_A-4291320 | rs2609264 | 90047103 | nonAB | 0.040104616 | C | T |
| SNP_A-2284008 | rs2609261 | 90054508 | BB | 0.198209042 | A | G |
| SNP_A-2152738 | rs1458553 | 90055014 | nonAA | 0.32632219 | A | G |
| SNP_A-2190887 | rs2609260 | 90055842 | nonAB | 0.660268059 | A | G |
| SNP_A-1824897 | rs10008568 | 90073215 | nonAB | 0.073628051 | A | G |
| SNP_A-2094935 | rs2464526 | 90098686 | AA | 0.148471845 | A | G |
| SNP_A-4284617 | rs2904259 | 90104737 | AA | 0.085423976 | C | T |
| SNP_A-1830961 | rs2609266 | 90106817 | AA | 0.124904291 | C | T |
| SNP_A-1977995 | rs1921679 | 90109807 | AA | 0.124831097 | A | G |
| SNP_A-4264355 | rs2178583 | 90110165 | AA | 0.275411131 | A | T |
| SNP_A-1977996 | rs2178584 | 90110221 | BB | 0.162876336 | C | T |
| SNP_A-2032491 | rs10033484 | 90124495 | AA | 0.216398627 | A | G |
| SNP_A-1832183 | rs7697075 | 90127331 | AA | 0.196280013 | A | G |

[1]Official SNP nomenclature according to NCBI db SNP version 126, May 2006.
[2]Chromosomal position based on the NCBI Build 36.1, March 2006.
[3]P value of genotype having highest QT values versus all other genotypes.

A genotype of TT at the rs3775378 locus was found to most accurately predict a predisposition to QT prolongation. This genotype is included amongst all genotypes associated with a predisposition to QT prolongation. Therefore, individuals having a genotype of TT at the rs3775378 locus may be considered predisposed to QT prolongation following the administration of a compound capable of prolonging the QT interval.

Since the QT interval changes with changes in heart rate, the QT interval is often measured as a corrected QT (QTc) interval. Any number of formulas may be employed to calculate the QTc, including, for example, the Fridericia formula (QTcF), the Bazett formula (QTcB), and the Rautaharju formula (QTp), among others. In the studies described herein, QT was calculated using the Fridericia formula. However, the present invention includes the use of any such formula or method for calculating a QTc or an uncorrected QT.

As noted above, a large number of compounds are known or suspected to be capable of inducing QT prolongation in some individuals, including individuals not suffering from LQTS. Such compounds may include compounds of Formula (1):

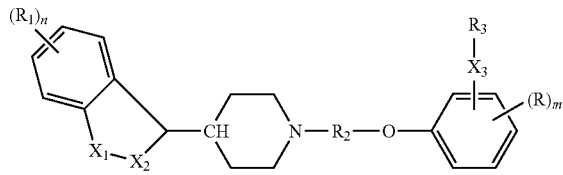

(1)

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

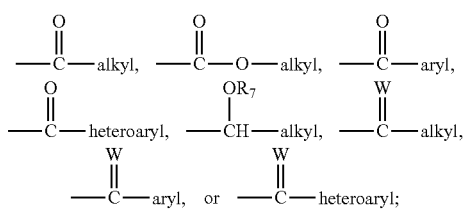

alkyl is lower alkyl, branched or straight and saturated or unsaturated;

acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is a five- or six-membered aryl ring having at least one heteroatom, $Q_3$, wherein each $Q_3$ is, independently, —O—, —S—, —N(H)—, or —C(H)=N—

W is $CH_2$ or $CHR_8$ or N—$R_9$;

$R_1$ is —H, lower alkyl, —OH, halo, lower alkoxy, trifluormethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

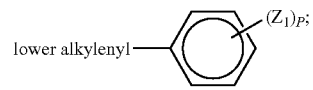

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

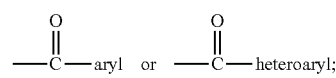

$X_1$, $X_2$, and $X_3$ are, independently, —O—, —S—, =N—, or —N($R_3$)—, or $X_1$ and $X_2$ are not covalently bound to each other and are, independently, —OH, =O, —$R_3$, or =$NR_3$;

lower is 1-4 carbon atoms;

m is 1, 2, or 3; and n is 1 or 2.

The compound may further include a compound of Formula (1), wherein:

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are =O, —OH, =N—, or —O—;

$R_2$ is $C_2$-$C_4$ alkylene or alkenylene;

$R_3$ is hydrogen, methyl, or ethyl;

$X_3$ is —O—; and

R is Formula (1A):

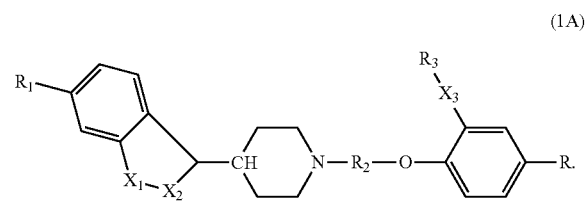

(1A)

In a further embodiment, the compound may be iloperidone, which is also referred to as 1-[4-[3-[4-(6-fluoro-1,2-benzisoxazol-3-yl)-1-piperidinyl]propoxy]-3-methoxyphenyl]ethanone, as shown in Formula 1B:

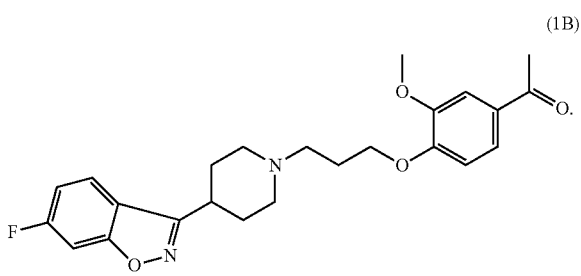 [SMILES: COc1cc(C(C)=O)ccc1OCCCN1CCC(c2noc3cc(F)ccc23)CC1]

(1B)

Iloperidone is disclosed in U.S. Pat. Nos. 5,364,866, 5,658,911, and 6,140,345, each of which is incorporated herein by reference. Metabolites of iloperidone may also be capable of prolonging a QT interval. Metabolites of Iloperidone, e.g., 1-[4-[3-[4-(6-Fluoro-1,2-benzisoxazol-3-yl)-1-piperidinyl]propoxy]-3-methoxyphenyl]ethanol, as shown in Formula 1C:

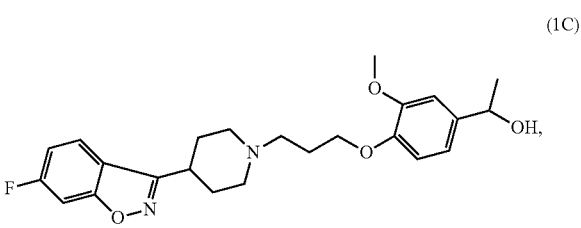 [SMILES: COc1cc(C(C)O)ccc1OCCCN1CCC(c2noc3cc(F)ccc23)CC1]

(1C)

are described in International Patent Application Publication No. WO03020707, which is also incorporated herein by reference.

Other iloperidone metabolites include: 1-[4-[3-[4-(6-Fluoro-1,2-benzisoxazol-3-yl)-1-piperidinyl]propoxy]-3-hydroxyphenyl]ethanone; 1-[4-[3-[4-(6-Fluoro-1,2-benzisoxazol-3-yl)-1-piperidinyl]propoxy]-3-methoxyphenyl]-2-hydroxyethanone; 4-[3-[4-(6-Fluoro-1,2-benzisoxazol-3-yl)-1-piperidinyl]propoxy]-3-hydroxy-α-methylbenzenemethanol; 4-[3-[4-(6-Fluoro-1,2-benzisoxazol-3-yl)-1-piperidinyl]propoxy]-2-hydroxy-5-methoxy-α-methylbenzenemethanol; 1-[4-[3-[4-(6-Fluoro-1,2-benzisoxazol-3-yl)-1-piperidinyl]propoxy]-2-hydroxy-5-methoxyphenyl]ethanone; and 1-[4-[3-[4-(6-Fluoro-1,2-benzisoxazol-3-yl)-1-piperidinyl]propoxy]-2,5-dihydroxyphenyl]ethanone. See U.S. Pat. No. 5,364,866 and International Patent Application Publication Nos. WO9309276 and WO9511680, which are incorporated herein by reference.

Using the genotypes at the SNP loci above, it is possible, with a high degree of certainty, to predict an individual's predisposition to QT prolongation. Table 2 below shows the results of a study of 174 individuals, each of whom was genotyped at the rs3775378 locus and their QT interval measured following the oral administration of 24 mg/day B.I.D. of iloperidone for a period of two weeks.

As can be seen in Table 2, an individual's FAM13A1 sequence at the SNP_A-1906173, rs3775378 locus is highly predictive of whether the individual will experience QT prolongation following the administration of iloperidone. For example, using the lowest threshold of a change in QTc interval (between baseline and the end of the second week) greater than 5 milliseconds (normal QTc intervals are between 0.30 and 0.44 seconds for males and between 0.30 and 0.45 for females), 9 of those individuals with the TT genotype (test is considered positive if the genotype for SNP_A-1906173, rs3775378 is TT) experienced QT prolongation while no such individuals did not. The resulting sensitivity (probability that the individual will have a SNP genotype associated with a predisposition to QT prolongation, given that he/she experienced QT prolongation) of 0.08, specificity (probability that the individual will not have a SNP genotype associated with a predisposition to QT prolongation, given that he/she did not experience QT prolongation) of 1.0, negative predictive value (probability that the individual will not experience QT prolongation, given that he/she does not have a SNP genotype associated with a predisposition to QT prolongation) of 0.38, and a positive predictive value (probability that the individual will experience QT prolongation, given that he/she has a SNP genotype associated with a predisposition to QT prolongation) of 1.0, permit one to predict with great accuracy that an individual possessing the TT genotype is likely to experience QT prolongation.

The use of higher thresholds (i.e., QTs greater than 15 and 30 milliseconds) yielded markedly increased negative predictive values (0.64 and 0.87, respectively). The associated decrease in positive predictive values, from 1.0 for QTs greater than 5 milliseconds to 0.67 for QTs greater than 30 milliseconds) suggests that additional factors affect more severe QT prolongation.

As the data in Table 2 show, an individual's FAM13A1 sequence at the SNP loci above may be used to predict whether an individual is predisposed to QT prolongation due to the administration of a compound capable of prolonging the QT interval. That is, individuals having a genotype of TT at the rs3775378 locus may reliably be predicted to experience a prolonged QT interval (i.e., a change in QT interval of at least 5 milliseconds) following the administration of a compound capable of prolonging the QT interval. Similarly, individuals having a genotype other than TT at the rs3775378 locus may reliably be predicted to not experience severe QT prolongation (i.e., a change in QT interval of greater than 15 milliseconds) following the administration of a compound capable of prolonging the QT interval.

The ability to make such predictions may be used in deciding whether to treat an individual with a particular compound and/or in determining the dosage appropriate for the individual. For example, an individual predicted to experience QT prolongation may be treated with an alter-

TABLE 2

QT Prolongation and Presence or Absence of a Genotype for SNP_A-1906173, rs3775378 Associated with a Predisposition to QT Prolongation

| Change Threshold | Low QT | | High QT | | | | | | negative predicitve | positive predictive |
|---|---|---|---|---|---|---|---|---|---|---|
| (msec) | −test | +test | −test | +test | Ratio | p value | sensitivity | specificity | value | value |
| QT > 5 | 63 | 0 | 101 | 9 | | 0.9741 | 0.08 | 1.00 | 0.38 | 1.00 |
| QT > 15 | 105 | 1 | 59 | 8 | 14.24 | 0.0133 | 0.12 | 0.99 | 0.64 | 0.89 | native compound not known or suspected to cause QT prolongation or may be administered a lower dose of a compound capable of causing QT prolongation than would be administered to an individual not predicted to experience QT prolongation.

The present invention also includes the administration of another compound useful in treating LQTS, in addition to one or more of the compounds above. Compounds useful in treating LQTS and/or preventing cardiac events resulting from LQTS, include, for example, beta blockers, such as propranolol, nadolol, atenolol, metoprolol.

The present invention also includes the prediction of an individual's predisposition for QT prolongation based on one or more of the SNP loci above in combination with the individual's genotype or gene sequence at one or more additional genes or loci. For example, International Patent Application Publication No. WO2006039663, incorporated herein by reference, describes a method of treating an individual with a compound capable of inducing QT prolongation based on the individual's CYP2D6 genotype. Other genotypes and/or gene sequences may similarly be used in combination with the SNP loci above, including those associated with LQTS. It should also be understood that the present invention includes the characterization of an expression product of the FAM13A1 gene rather than, or in addition to, the determination of one or more SNP genotypes within the FAM13A1 gene. For example, by determining a sequence of an mRNA strand transcribed from the FAM13A1 gene, it is possible to determine the sequence of the FAM13A1 gene itself and, as described above, determine whether the FAM13A1 gene sequence is associated with a predisposition to QT prolongation.

Similarly, by properly characterizing a functional peptide or protein, including the FAM13A1 enzyme, translated from the mRNA strand above, it is possible to determine the sequence of the FAM13A1 gene itself and, as described above, determine whether the FAM13A1 gene sequence is associated with a predisposition to QT prolongation. In addition, the present invention includes determining whether a compound is capable of prolonging a QT interval in an individual. This may be done, for example, by measuring a change in QT interval in a test organism (e.g., human, animal model, cell line) known to possess a FAM13A1 genotype associated with a predisposition to QT prolongation following the administration of a quantity of compound under study.

Preferably, the compound is also administered to a test organism known to possess a FAM13A1 genotype not associated with a predisposition to QT prolongation.

Thus, in addition to other illustrative embodiments, this invention can be seen to comprise one or more of the following illustrative embodiments:
1. A method of administering to an individual a compound capable of prolonging the individual's QT interval, the method comprising:
    determining at least a portion of an individual's FAM13A1 (family with sequence similarity 13, member A1) gene sequence; and
    in the case that a portion of the individual's FAM13A1 gene sequence is associated with an increased risk of QT prolongation, administering to the individual a quantity of the compound less than would be administered to an individual having a FAM13A1 gene sequence not associated with an increased risk of QT prolongation.
2. The method of embodiment 1, wherein determining includes determining the individual's genotype at the rs3775378 locus.
3. The method of embodiment 2, wherein the genotype associated with an increased risk of QT prolongation is TT.
4. The method of embodiment 1, further comprising: determining the individual's CYP2D6 genotype.
5. The method of embodiment 1, wherein the compound is selected from a group consisting of: amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, thioridazine; alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, ziprasidone; albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, trimipramine, and metabolites, pharmaceutically-acceptable salts, and combinations thereof.
6. The method of embodiment 5, wherein the compound has the formula:

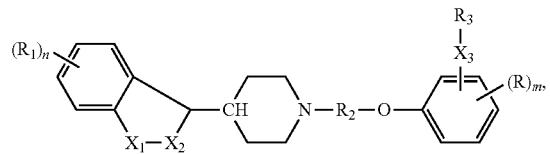

wherein: R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

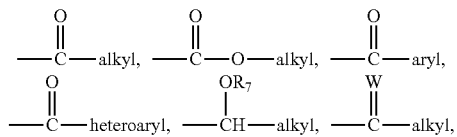

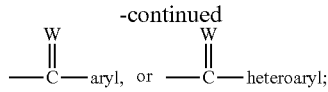

alkyl is lower alkyl, branched or straight and saturated or unsaturated;

acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is is a five- or six-membered aryl ring having at least one heteroatom, $Q_3$, wherein each $Q_3$ is, independently, —O—, —S—, —N(H)—, or —C(H)=N—

W is $CH_2$ or $CHR_8$ or N—$R_9$;

$R_1$ is —H, lower alkyl, —OH, halo, lower alkoxy, trifluoromethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

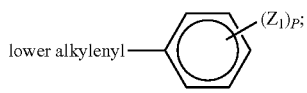

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

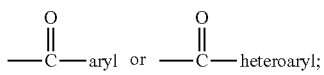

$X_1$, $X_2$, and $X_3$ are, independently, —O—, —S—, =N—, or —N($R_3$)—, or $X_1$ and $X_2$ are not covalently bound to each other and are, independently, —OH, =O, —$R_3$, or =$NR_3$; lower is 1-4 carbon atoms;

m is 1, 2, or 3; and n is 1 or 2.

7. The method of embodiment 6, wherein:

R is —C(O)CH$_2$OH, —CH(OH)C(O)CH$_2$OH, —C(O)OH, CH(OH)CH$_3$, or C(O)CH$_3$;

$R_1$ is halo;

$X_1$ and $X_2$ are different and are =O, —OH, =N—, or —O—;

$R_2$ is $C_2$-$C_4$ alkylene or alkenylene;

$R_3$ is hydrogen, methyl, or ethyl;

$X_3$ is —O—;

R is

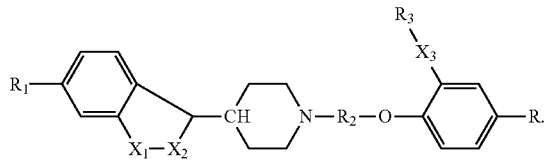

8. The method of embodiment 7, wherein the compound of Formula 1 is 1-[4-3-[4-(6-fluoro-1,2-benzisoxazol-3-yl)-1-piperidinyl]propoxy]-3-methoxyphenyl]ethanone, as shown in Formula 1B:

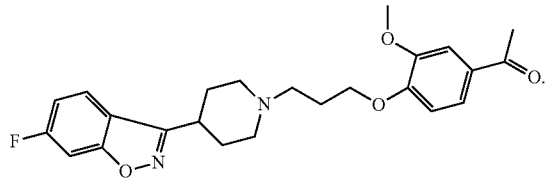

9. The method of embodiment 7, wherein the compound of Formula 1 is 1-[4-[3-[4-(6-Fluoro-1,2-benzisoxazol-3-yl)-1-piperidinyl]propoxy]-3-methoxyphenyl]ethanol, as shown in Formula 1C:

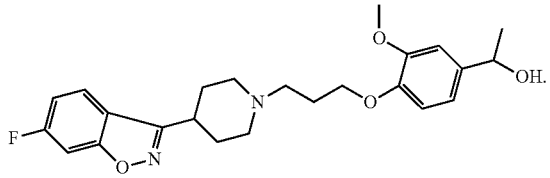

10. A method of determining whether an individual is predisposed to prolongation of the QT interval, the method comprising:
    determining at least a portion of an individual's FAM13A1 (family with sequence similarity 13, member A1) gene sequence.

11. The method of embodiment 10, further comprising:
    in the case that a portion of the individual's FAM13A1 gene sequence is associated with an increased risk of QT prolongation, administering to the individual a compound not known or suspected to cause QT prolongation.

12. The method of embodiment 10, wherein determining includes determining the individual's genotype at the rs3775378 locus.

13. The method of embodiment 12, wherein the genotype associated with an increased risk of QT prolongation is TT.

14. The method of embodiment 10, further comprising:
    determining the individual's CYP2D6 genotype.

15. A method of administering a compound capable of prolonging a QT interval to an individual suffering from long QT syndrome (LQTS), the method comprising:
    determining at least a portion of an individual's FAM13A1 (family with sequence similarity 13, member A1) gene sequence; and administering to the individual a quantity of the compound based on the individual's FAM13A1 gene sequence.

16. The method of embodiment 15, wherein determining includes determining the individual's genotype at the rs3775378 locus.

17. The method of embodiment 16, wherein the genotype associated with an increased risk of QT prolongation is TT.

18. The method of embodiment 15, further comprising: determining the individual's CYP2D6 genotype.

19. The method of embodiment 15, wherein the compound is selected from a group consisting of: amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, thioridazine; alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, ziprasidone; albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, trimipramine, and metabolites, pharmaceutically-acceptable salts, and combinations thereof.

20. The method of embodiment 19, wherein the compound has the formula:

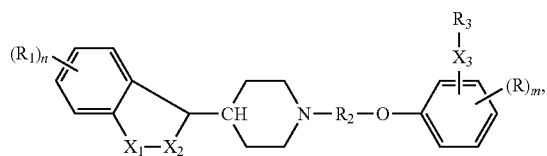

(1)

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

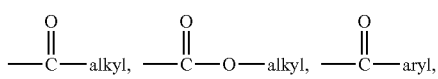

-continued

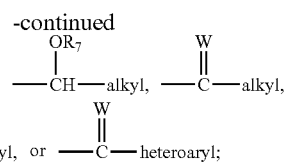

alkyl is lower alkyl, branched or straight and saturated or unsaturated;

acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is a five- or six-membered aryl ring having at least one heteroatom, $Q_3$, wherein each $Q_3$ is, independently, —O—, —S—, —N(H)—, or —C(H)=N—

W is $CH_2$ or $CHR_8$ or N—$R_9$;

$R_1$ is —H, lower alkyl, —OH, halo, lower alkoxy, trifluormethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

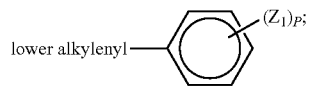

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

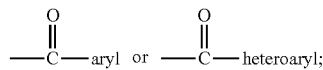

$X_1$, $X_2$, and $X_3$ are, independently, —O—, —S—, =N—, or —N($R_3$)—, or $X_1$ and $X_2$ are not covalently bound to each other and are, independently, —OH, =O, —$R_3$, or =$NR_3$; lower is 1-4 carbon atoms;

m is 1, 2, or 3; and n is 1 or 2.

21. The method of embodiment 20, wherein:

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are =O, —OH, =N—, or —O—;

$R_2$ is $C_2$-$C_4$ alkylene or alkenylene;

$R_3$ is hydrogen, methyl, or ethyl;

$X_3$ is —O—;

R is

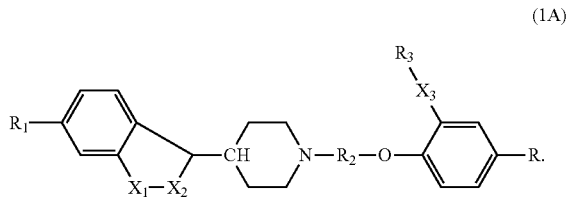
(1A)

22. The method of embodiment 21, wherein the compound of Formula 1 is 1-[4-3-[4-(6-fluoro-1,2-benzisoxazol-3-yl)-1-piperidinyl]propoxy]-3-methoxyphenyl]ethanone, as shown in Formula 1B:

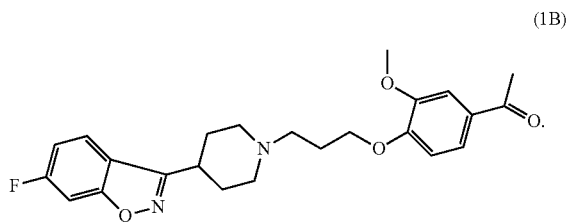 [SMILES: COc1cc(C(C)=O)ccc1OCCCN1CCC(c2noc3cc(F)ccc23)CC1]
(1B)

23. The method of embodiment 21, wherein the compound of Formula 1 is 1-[4-[3-[4-(6-Fluoro-1,2-benzisoxazol-3-yl)-1-piperidinyl]propoxy]-3-methoxyphenyl]ethanol, as shown in Formula 1C:

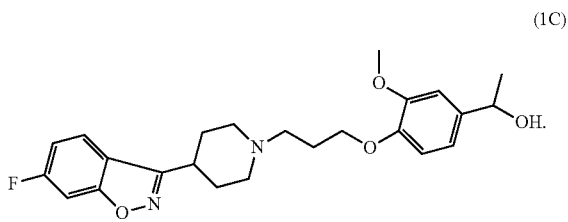 [SMILES: COc1cc(C(C)O)ccc1OCCCN1CCC(c2noc3cc(F)ccc23)CC1]
(1C)

24. A method of administering to an individual a compound capable of prolonging the individual's QT interval, the method comprising:
  characterizing an expression product of an individual's FAM13A1 (family with sequence similarity 13, member A1) gene; and
  in the case that the characterized expression product is associated with an increased risk of QT prolongation, administering to the individual a quantity of the compound less than would be administered to an individual having an expression product not associated with an increased risk of QT prolongation.

25. The method of embodiment 24, wherein the expression product includes at least one expression product selected from a group consisting of: mRNA, a peptide, and a protein.

26. A method of determining whether an individual is predisposed to prolongation of the QT interval, the method comprising:
  characterizing an expression product of an individual's FAM13A1 (family with sequence similarity 13, member A1) gene.

27. The method of embodiment 26, wherein the expression product includes at least one expression product selected from a group consisting of: mRNA, a peptide, and a protein.

28. A method of administering a compound capable of prolonging a QT interval to an individual suffering from long QT syndrome (LQTS), the method comprising:
  characterizing an expression product of an individual's FAM13A1 (family with sequence similarity 13, member A1) gene; and
  administering to the individual a quantity of the compound based on the characterized expression product.

29. The method of embodiment 28, wherein the expression product includes at least one expression product selected from a group consisting of: mRNA, a peptide, and a protein.

30. A method of determining whether a compound is capable of prolonging a QT interval in an individual, the method comprising:
  measuring an expression product of the individual's FAM13A1 (family with sequence similarity 13, member A1) gene;
  administering to the individual a quantity of the compound;
  re-measuring the expression product of the individual's FAM13A1 gene; and
  determining whether the compound is capable of prolonging the individual's QT interval based on a difference in the measurements of the expression product of the individual's FAM13A1 gene.

31. The method of embodiment 30, wherein the expression product includes at least one expression product selected from a group consisting of: mRNA, a peptide, and a protein.

32. A method of determining whether a compound is capable of prolonging a QT interval in an individual, the method comprising:
  measuring a QT interval of each of a plurality of test organisms, the plurality including a first test organism having a FAM13A1 (family with sequence similarity 13, member A1) genotype associated with a predisposition for prolongation of QT interval and a second organism having a FAM13A1 genotype not associated with a predisposition for prolongation of QT interval;
  administering a quantity of the compound to each of the plurality of test organisms;
  re-measuring a QT interval of at least the first test organism; and
  determining that the compound is capable of prolonging a QT interval in an individual in the case that the re-measured QT interval is greater than the measured QT interval.

33. The method of embodiment 32, wherein each of the plurality of test organisms is selected from a group consisting of: humans, animals, and cell lines.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:
1. A method of administering a compound to a human individual, wherein the compound is iloperidone, a metabo- lite of iloperidone, or a pharmaceutically acceptable salt of iloperidone or metabolite thereof, the method comprising:

determining the individual's FAM13A1 (family with sequence similarity 13, member A1) genotype at a single nucleotide polymorphism (SNP) locus selected from the group consisting of rs17014687, rs17014546, rs6814344, rs13131633, and rs4544678; and administering a first quantity of the compound if the individual's FAM13A1 genotype is associated with increased risk of QT prolongation and is TT at rs17014687, non-CC at rs17014546, non-TT at rs6814344, non-GG at rs13131633, or non-AA at rs4544678, or administering a second quantity of the compound if the individual's FAM13A1 genotype is non-TT at rs17014687, CC at rs17014546, TT at rs6814344, GG at rs13131633, or AA at rs4544678; wherein the first quantity of the compound is less than the second quantity of the compound.

2. The method of claim 1, further comprising determining the individual's CYP2D6 genotype.

3. The method of claim 1, wherein the compound is iloperidone or a pharmaceutically acceptable salt thereof.

4. A method of administering a compound to a human individual suffering from long QT syndrome (LQTS), wherein the compound is iloperidone, a metabolite of iloperidone, or a pharmaceutically acceptable salt of iloperidone or metabolite thereof, the method comprising:

determining the individual's FAM13A1 (family with sequence similarity 13, member A1) genotype at a single nucleotide polymorphism (SNP) locus selected from the group consisting of rs17014687, rs17014546, rs6814344, rs13131633, and rs4544678; and administering a first quantity of the compound if the individual's FAM13A1 genotype is associated with increased risk of QT prolongation and is TT at rs17014687, non-CC at rs17014546, non-TT at rs6814344, non-GG at rs13131633, or non-AA at rs4544678, or administering a second quantity of the compound if the individual's FAM13A1 genotype is non-TT at rs17014687, CC at rs17014546, TT at rs6814344, GG at rs13131633, or AA at rs4544678; wherein the first quantity of the compound is less than the second quantity of the compound.

5. The method of claim 4, further comprising determining the individual's CYP2D6 genotype.

6. The method of claim 4, wherein the compound is iloperidone or a pharmaceutically acceptable salt thereof.

7. The method of claim 1, wherein the compound is a metabolite of iloperidone, wherein the metabolite is 1-[4-[3-[4-(6-Fluoro-1,2-benzisoxazol-3-yl)-1-piperidinyl]propoxy]-3-methoxyphenyl]ethanol, or a pharmaceutically acceptable salt thereof.

8. The method of claim 4, wherein the compound is a metabolite of iloperidone, wherein the metabolite is 1-[4-[3-[4-(6-Fluoro-1,2-benzisoxazol-3-yl)-1-piperidinyl]propoxy]-3-methoxyphenyl]ethanol, or a pharmaceutically acceptable salt thereof.

9. The method of claim 1, wherein the second quantity of the compound is 24 mg/day.

10. The method of claim 4, wherein the second quantity of the compound is 24 mg/day.

* * * * *